(12) United States Patent
Noda et al.

(10) Patent No.: US 8,647,352 B2
(45) Date of Patent: Feb. 11, 2014

(54) DEVICES AND METHODS FOR SECURING TISSUE

(75) Inventors: Wayne A. Noda, Mission Viejo, CA (US); Stephen Graham Bell, Rome (IT)

(73) Assignee: Insightra Medical, Inc., Irvine, CA (US)

(*) Notice: Subject to any disclaimer, the term of this patent is extended or adjusted under 35 U.S.C. 154(b) by 21 days.

(21) Appl. No.: 13/301,188

(22) Filed: Nov. 21, 2011

(65) Prior Publication Data
US 2012/0065582 A1 Mar. 15, 2012

Related U.S. Application Data

(62) Division of application No. 12/141,391, filed on Jun. 18, 2008, now Pat. No. 8,062,308.

(60) Provisional application No. 61/012,124, filed on Dec. 7, 2007, provisional application No. 60/982,083, filed on Oct. 23, 2007.

(51) Int. Cl.
*A61B 17/12* (2006.01)
*A61B 17/122* (2006.01)

(52) U.S. Cl.
USPC ........... 606/140; 606/141; 606/206; 128/831; 29/235

(58) Field of Classification Search
USPC .............. 606/141, 206, 140; 128/831; 29/235
See application file for complete search history.

(56) References Cited

U.S. PATENT DOCUMENTS

| 4,167,188 A | 9/1979 | Lay et al. | |
| 5,356,416 A * | 10/1994 | Chu et al. | 606/140 |
| 6,613,060 B2 * | 9/2003 | Adams et al. | 606/140 |
| 2002/0183767 A1 | 12/2002 | Adams et al. | |
| 2003/0069488 A1 | 4/2003 | Alferness et al. | |

FOREIGN PATENT DOCUMENTS

GB 649226 1/1951

* cited by examiner

*Primary Examiner* — Vy Q Bui
(74) *Attorney, Agent, or Firm* — John L. Rogitz; John M. Rogitz

(57) ABSTRACT

A compression ring to grip and compress body structure such as diverticulum, hemorrhoids, and tissue adjacent a hole. A resilient ring-shaped body defines a compression channel, and one or more axially rigid elongated spikes extend from the body into the channel. The body defines a first axial segment surrounding the compression channel and a second axial segment surrounding the compression channel, with the spike being engaged only with the second axial segment. The first axial segment more tightly compresses the body structure than the second axial segment.

16 Claims, 10 Drawing Sheets

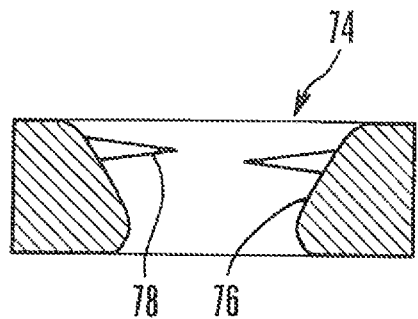
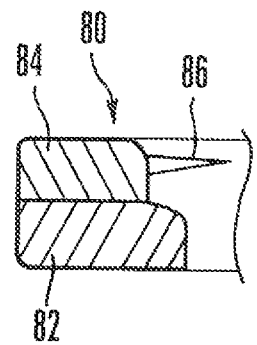
Figure 19    Figure 20
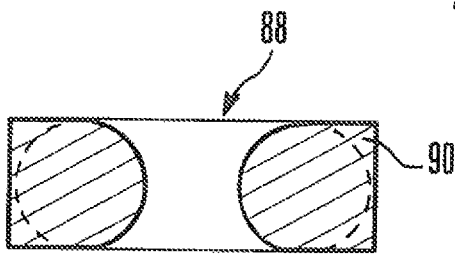
Figure 21
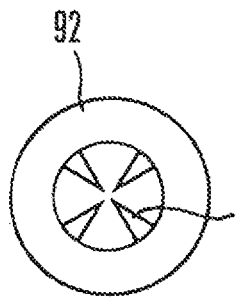  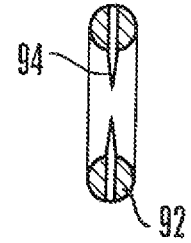  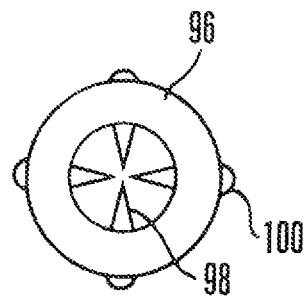
Figure 22    Figure 23    Figure 24
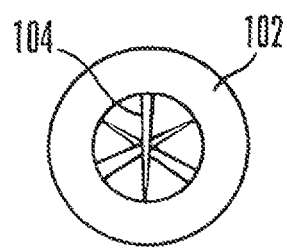  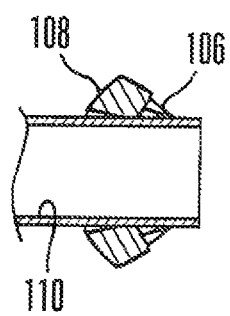
Figure 25    Figure 26

DEVICES AND METHODS FOR SECURING TISSUE

This is a divisional application of and which claims Priority to U.S. patent application Ser. No. 12/141,391 filed on Jun. 18, 2008 now U.S. Pat. No. 8,062,308 which claims priority to U.S. provisional application Ser. No. 61/012,124 filed Dec. 7, 2007, which claims priority to U.S. provisional application Ser. No. 60/982,083 filed Oct. 23, 2007.

FIELD OF THE INVENTION

The present application relates generally to devices and methods for securing inverted tissue, and more particularly, though not exclusively, to securing inverted diverticulum serosa to serosa.

BACKGROUND OF THE INVENTION

Diverticulosis is an unfortunately common condition in which an area of the intestine bilges out into the peritoneal cavity to form a sac referred to as a "diverticulum". Diverticulum are also formed when a point of weakness in the intestinal wall, e.g., where blood vessels take their entry, causes the muscular structure to divide and allows part of the inner mucosal membrane to be pushed out of the hole into the peritoneal cavity and become filled with fecal matter. Diverticulum may also be present in other parts of the gastrointestinal tract such as the esophagus or the duodenum. A burst or leaky diverticulum results in the release of contaminants into the peritoneal cavity, potentially causing peritonitis.

A natural orifice-based method for resolving diverticulum is disclosed in the present assignee's co-pending U.S. patent application Ser. No. 11/788,597, filed Apr. 20, 2007, incorporated herein by reference. As understood herein, a diverticulum may be inverted into the bowel and tied off and either resected into a tube or allowed to slough off using natural orifice principles to avoid the complications inherent in other surgical methods. As further understood herein, for optimal closing the inverted diverticulum ideally is closed off serosa to serosa. As still further recognized by present principles, a diverticulum preferably is tightly and securely held closed off to alleviate the risk of peritonitis.

SUMMARY OF THE INVENTION

A method for treating a diverticulum formed in an intestinal wall of a patient includes advancing an applicator such as a tube into the intestine through a natural orifice to the site of the divertictilum. The method also includes inverting the diverticulum using the tube, and clamping the diverticulum with a resilient ring having one or more spikes that engage the diverticulum.

In some embodiments, intestinal wall tissue adjacent the diverticulum is held by the ring serosa to serosa. The ring may include a round resilient body defining an axial through-opening configured to receive the diverticulum, with the spikes extending from the body into the through-opening. The body can be defined by first and second portions that are coaxial to each other and offset from each other in the axial dimension defined by the body. The first portion is configured to compress the diverticulum a first magnitude and the second portion is configured to compress the diverticulum a second magnitude, with the first magnitude being greater than the second magnitude. The spikes preferably are engaged with the second portion and no spike is engaged with the first portion. The ring is advanced onto the inverted diverticulum first portion first.

In some implementations, the first portion is defined by a first wall and the second portion is defined by a second wall, and the first wall is thicker than the second wall. In other implementations, the first portion is made of a first material and the second portion is made of a second material different than the first material.

The ring may be preloaded onto the tube and urged off the tube onto the diverticulum. Or, the rings can stay static and the tube retracted to release the rings. If desired, plural rings can be preloaded onto the tube. The ring can be preloaded onto the tube with the spike extending distal of the body, or the ring can be preloaded onto the tube with the spike extending proximal to the body. In some embodiments the ring is urged from a side opening in the tube onto the diverticulum.

The spikes may extend substantially across a diameter of the through-hole. Or, each spike may define an end disposed substantially in the center of the ring when the ring is relaxed. The ring may include tabs arranged on an outer periphery of the ring.

In still other embodiments, the spikes may be movable on the ring in the radial plane defined by the ring between a retracted position and an extended position. An actuating ring can be supplied to engage with the resilient ring to move the spike toward the extended position.

In another aspect, a tissue compressing device includes a round resilient body defining an axial central passage configured to receive tissue therein. At least one spike extends from the body into the central passage. The body is defined by at least first and second portions that are coaxial to each other and offset from each other in the axial dimension defined by the body. The first portion is configured to compress the diverticulum a first magnitude and the second portion is configured to compress the diverticulum a second magnitude, with the first magnitude being greater than the second magnitude.

In another aspect, a method for holding tissue together includes advancing into a patient through a natural orifice a closure ring including a resilient ring-shaped body defining a compression channel and at least one axially rigid elongated gripping element extending from the body into the channel. The method includes engaging the closure ring with body structure such that the gripping element penetrates the body structure and the body surrounds and compresses in the compression channel at least a part of the body structure. The body structure may be, without limitation, a diverticulum, a hemorrhoid, or tissue defining a tissue hole.

In another aspect, an apparatus includes a resilient ring-shaped body defining a compression channel. At least one axially rigid elongated gripping element extends from the body into the channel. The body defines a first axial segment surrounding the compression channel and a second axial segment surrounding the compression channel. The first axial segment is not engaged with the gripping element while the second axial segment is indeed engaged with the gripping element. The first axial segment more tightly compresses the body structure than the second axial segment.

A compression ridge can be molded into the ring, with the radius of curvature of the ridge being established as desired for achieving a desired rate of sloughing. A sharper ridge causes the tissue to slough off faster, while a less sharp-ridge allows greater time for serosa to serosa healing prior to sloughing.

The details of the present invention, both as to its structure and operation, can best be understood in reference to the accompanying drawings, in which like reference numerals refer to like parts, and in which:

BRIEF DESCRIPTION OF THE DRAWINGS

FIG. 19 is a cross-sectional view of an alternate compression ring;

FIG. 20 is a cross-sectional view of another alternate compression ring;

FIG. 21 is a cross-sectional view of yet another alternate compression ring;

FIG. 22 is a perspective view of a torus-shaped compression ring with four spikes;

FIG. 23 is a cross-sectional view of the ring shown in FIG. 22;

FIG. 24 is a perspective view of a compression ring with four spikes and optional manipulation tails on the outer periphery of the ring;

FIG. 25 is a perspective view of an alternate compression ring with overlapping spikes;

FIG. 26 is a partial cross-section of a compression ring loaded onto a delivery tube, with the spikes oriented distally on the tube;

DETAILED DESCRIPTION OF THE PREFERRED EMBODIMENT

Figure 1:
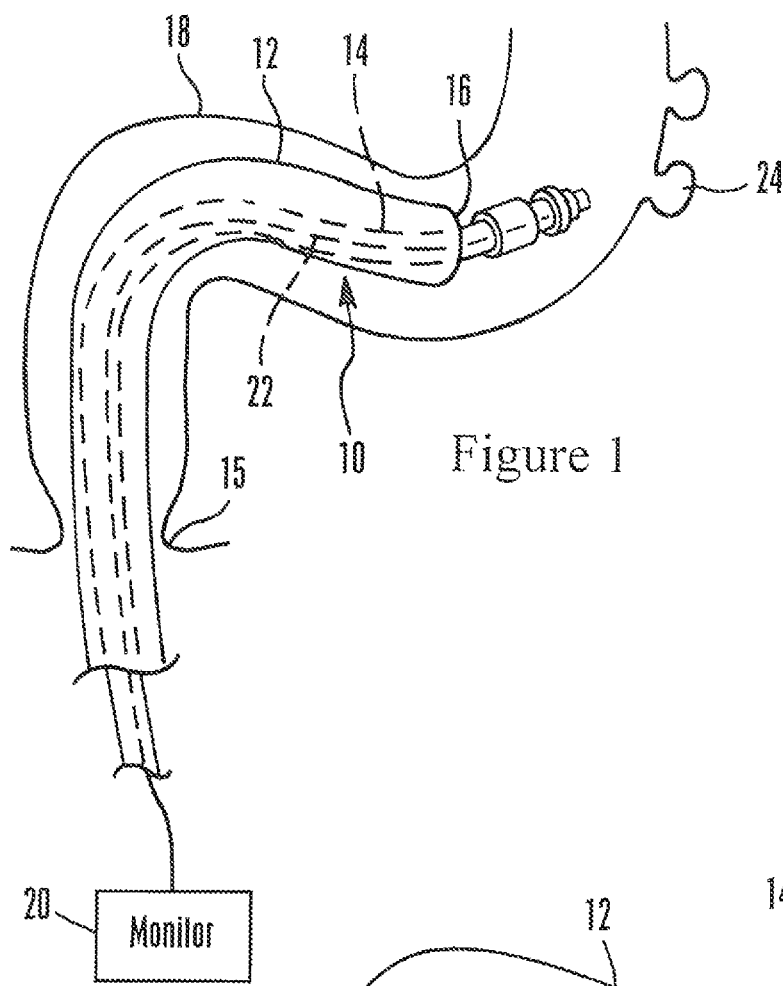
FIG. 1 is a schematic view showing a tissue compression ring deployment mechanism including an overtube and colonoscope being advanced through the anus into the colon.

Referring initially to FIG. 1, a catheter assembly is shown, generally designated 10, that includes a flexible hollow overtube 12 fixedly or slidably holding one or more components such as but not limited to an endoscope such as a colonoscope 14 that may have plural working channels. The overtube 12 may be transparent plastic. The overtube 12 with colonoscope 14 is configured for being advanced into the patient through a natural orifice, such as the anus 15. The colonoscope 14 may extend from the open distal end 16 of the overtube 12 as shown to a colonoscope control handle (not shown) that is external to the patient. In this way, for example, images of the colon 18 from the colonoscope 14 can be presented on a monitor 20 to a surgeon. Accordingly, it will be appreciated that the colonoscope 14 bears one or more light guides 22 such, as optical fibers for imaging the interior of the patient. The colonoscope 14 may extend through a working lumen of the overtube 12. Additional components may extend through additional working lumens and/or may be swapped according to the stage of the procedure for the colonoscope 14.

As intended herein, the overtube 12 can be flexible and, can be sized as appropriate for the patient, e.g., shorter and radially smaller overtubes can be provided for pediatric patients. Although not shown in FIG. 1, the open distal end 16 of the overtube 12 may be tapered into a frusto-conical shape to reduce the risk that parts of the colon wall may become trapped between the overtube 12 and the colonoscope 14 during advancement of the overtube 12. Also, the inner surface of the overtube 12 can be coated with a lubricious material to ensure smooth advancement of the overtube 12 over the colonoscope 14.

In one non-limiting procedure, the catheter assembly 10 is advanced through the anus 15 into the colon 18 to an area of diverticulum disease, i.e., to a diverticulum 24. Due to the nature and location of the diverticulum 24, the assembly 10 may be guided by an imaging system—optical or radiography (colonoscope, gastroscope, radiologically or a combination thereof). Alternatively, the catheter can be advanced into the small intestine through the esophagus, in which case upper GI imaging and enteroscopy may be used to guide the catheter. Present principles may also be employed to use the below-described compression rings to close off hemorrhoids, close openings in tissue, etc.

The overtube 12 is typically advanced together with the colonoscope 14. When the distal end 16 of the overtube 12 is kept behind the tip of the colonoscope 14, the colonoscope 14 has full maneuverability. During colonoscopy, air or some other gas may be used if desired to insufflate the otherwise collapsed colon.

To enhance locating diverticulum, a barium study can first be employed to ascertain the number and location of diverticulum prior to diverticuloectomy. Alternatively, contrast media can be flushed into the colonic lumen during colonoscopy.

Figure 2:
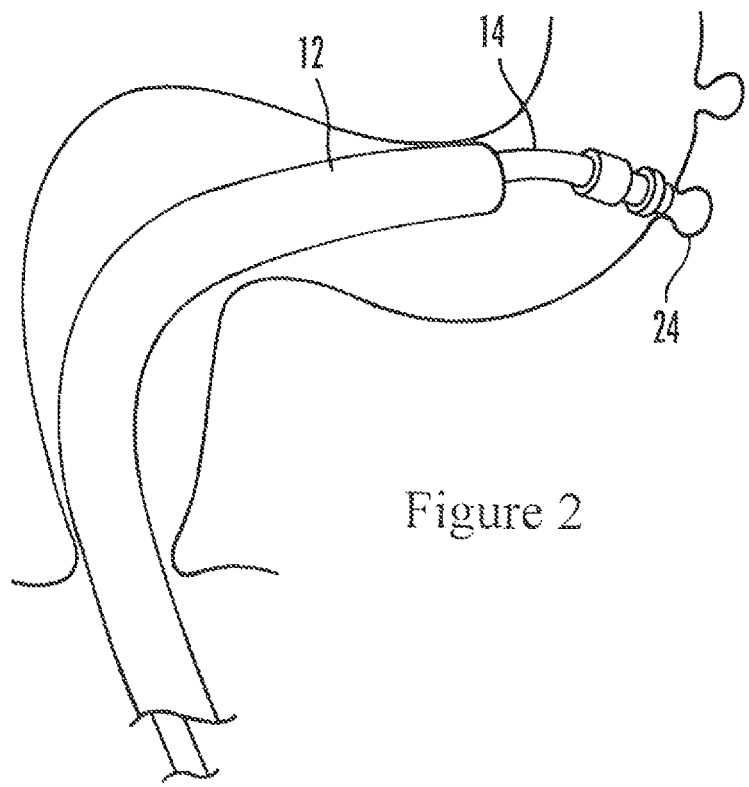
FIG. 2 is a schematic view showing the colonoscope advanced to a diverticulum.
Figure 3:
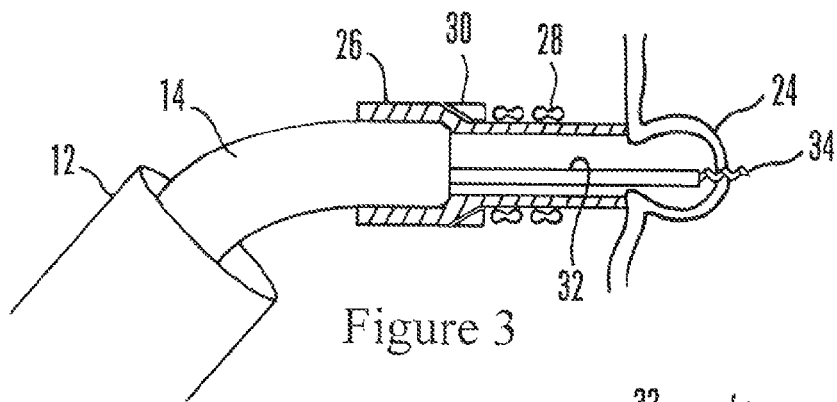
FIG. 3 is a schematic view in partial cross-section showing a grasper being advanced out of the colonoscope into the diverticulum.

Turning to FIG. 2, the overtube 12 is positioned adjacent to a diverticulum 24 and then the colonoscope 14 advanced to the diverticulum 24 as shown. Referring to FIG. 3, the distal end of the colonoscope 14 may be formed with or engaged with a load collar 26 that bears one or more compression rings 28, as well as, in some embodiments, a pushing element 30 for pushing the rings 28 one at a time off the collar 26 as either the pushing element is slid distally on the scope or the scope is pulled proximally relative to the pushing element. With the distal end of the collar 26 forming a seal against tissue surrounding the diverticulum, if desired a vacuum may be established in the colonoscope 14 to urge the diverticulum into the colonoscope. When a separate applicator other than the scope is used, this comment applies to the separate applicator. Additionally or in lieu of a vacuum, an applicator such as but not limited to an inversion tube 32 may be advanced out of a working channel of the colonoscope 14 and into the diverticulum 24, and gripping structure such as a corkscrew element 34 used to grip the diverticulum 24.

Figure 4:
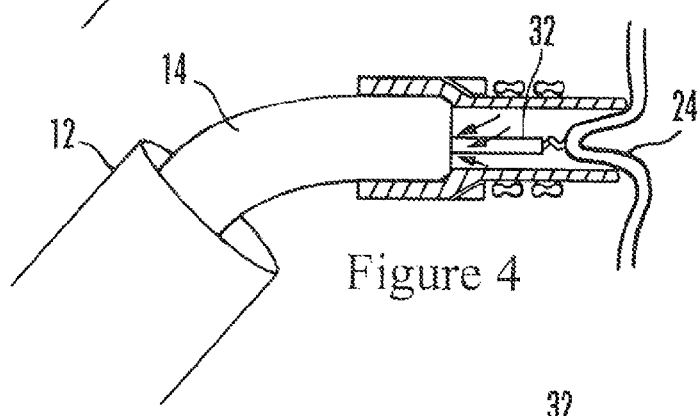
FIG. 4 is a schematic view in partial cross-section showing the grasper being retracted to invert the diverticulum, possibly aided by vacuum.
Figure 5:
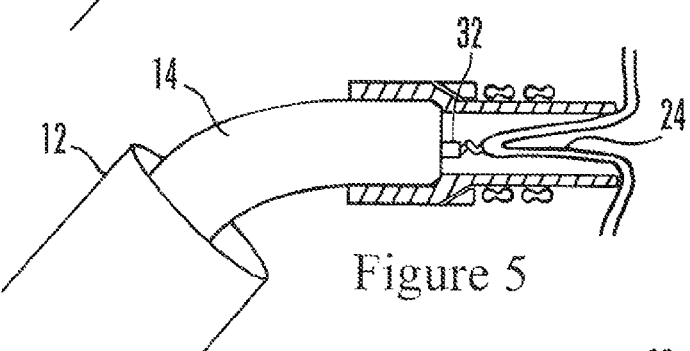
FIG. 5 is a schematic view in partial cross-section showing the grasper being retracted to more fully invert the diverticulum.

FIGS. 4 and 5 show successive locations of the diverticulum 24 as the inversion tube 32 is retracted (and/or as vacuum is drawn in the colonoscope 14), inverting the diverticulum 24 into the colonoscope 14. Then, the pushing element 30 is actuated to push the distal-most compression ring 28 onto the diverticulum 24 as shown, with substantially all of the diverticulum 24 pulled proximal to the ring 28.

Figure 6:
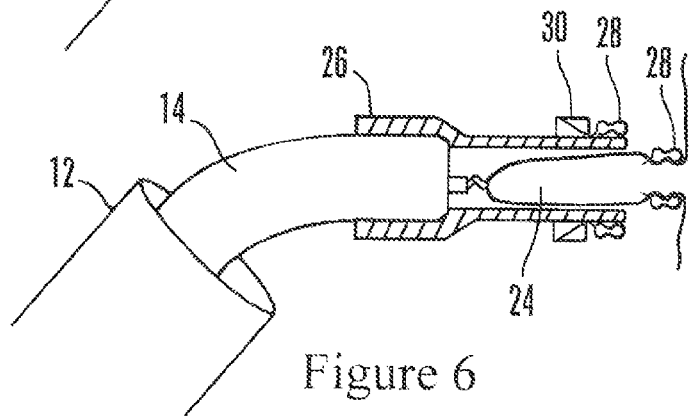
FIG. 6 is a schematic view in partial cross-section showing a compression ring just after it has been pushed off the end of the colonoscope onto the inverted diverticulum.
Figure 7:
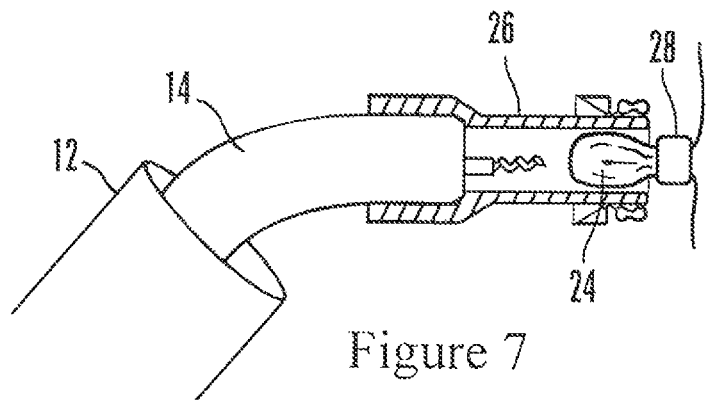
FIG. 7 is a schematic view in partial cross-section showing the compression ring on the inverted diverticulum in full side view.

It is now to be appreciated that in the relaxed state, the ring 28 assumes a radially smaller configuration (as shown for the distal-most ring 28 in FIG. 6 as engaged with the diverticulum), and is resilient so that it can be stretched to a radially enlarged state to fit onto the collar 26 (as shown for the proximal ring 28 in FIG. 6). FIG. 7 shows that in side view, the ring 28 that engages the diverticulum 24 surrounds and compresses the diverticulum 24. Because the diverticulum 24 is compressed in its inverted state, it is closed off serosa to serosa. Further details of example embodiments of the compression ring 28 are set forth further below.

Figure 8:
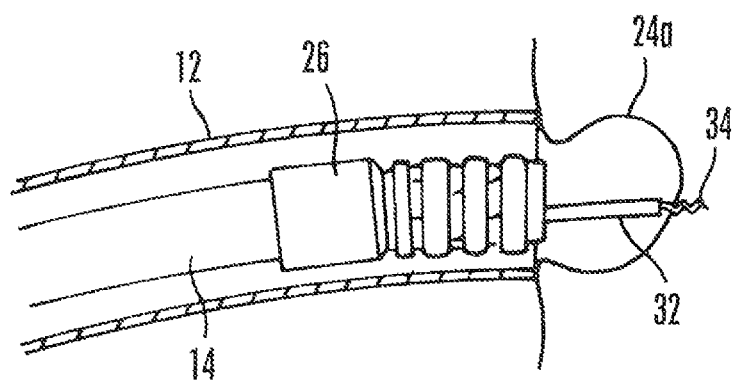
FIG. 8 is a schematic view in partial cross-section showing a grasper being advanced out of the colonoscope into a relatively large diverticulum in which the overtube is advanced against the surrounding colonic wall and evacuated.

FIG. 8 shows that for a relatively large diverticulum 24a, instead of inversion by evacuating the colonoscope 14, the overtube 12 may be positioned against tissue surrounding the diverticulum 24a and evacuated to aid in inverting the diverticulum 24a.

Figure 9:
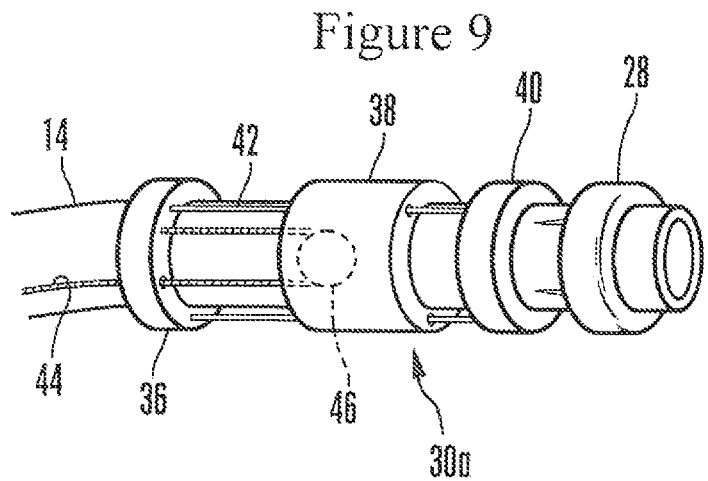
FIG. 9 is a perspective view of a non-limiting colonoscope with pre-loaded compression ring, illustrating one mechanism to push the ring off the scope, with the proximal portions of the scope cut away for clarity.

FIG. 9 shows an example non-limiting embodiment of the pushing element 30. While the pushing element 30 of FIG. 9 envisions the pushing element 30 moving distally to push the rings 28 off the distal end of the colonoscope 14 as the colonoscope 14 remains stationary, in other implementations the pushing element 30 may simply prevent the rings 28 from moving with the colonoscope 14 as the colonoscope 14 is retracted proximally. Additional details of non-limiting example pushing elements that may be used are disclosed in the following U.S. patents, incorporated herein by reference: U.S. Pat. Nos. 5,320,630; 5,423,834; 5,423,834; 5,735,861; 5,462,559; 5,624,453; 6,007,551; 6,149,659; 6,565,578.

As shown in FIG. 9, in one specific example of the pushing element 30 designated 30a in FIG. 9, a movable proximal ring 36 can slide on the colonoscope 14 and an anchor ring 38 can be affixed to the colonoscope 14. The pushing element 30a can also include a movable distal ring 40 that can slide on a reduced diameter extension of the anchor ring 38.

One or more axially rigid push rods 42 extend from the proximal ring 36, through respective channels of the anchor ring 38, and to the distal ring 40. A flexible actuating wire or cord 44 has its proximal end (not shown) disposed outside the patient and its distal end affixed to the proximal ring 36 as shown. The wire or cord 44 extends around a pulley element 46 (shown in phantom in FIG. 9) that is engaged with the anchor ring 38.

With this structure, it may readily be appreciated that the wire or cord 44 can be pulled proximally to move the proximal ring 36 distally on the colonoscope 14. In turn, owing to the axially rigid push rods 42, the distal ring 40 is moved distally against the compression rings 28, pushing the distal-most compression ring 28 off the end of the colonoscope 14. Once released, the compression ring assumes the relaxed, radially smaller configuration discussed above in which the compression ring 28 surrounds and compresses tissue such as the diverticulum 24.

Figure 10:
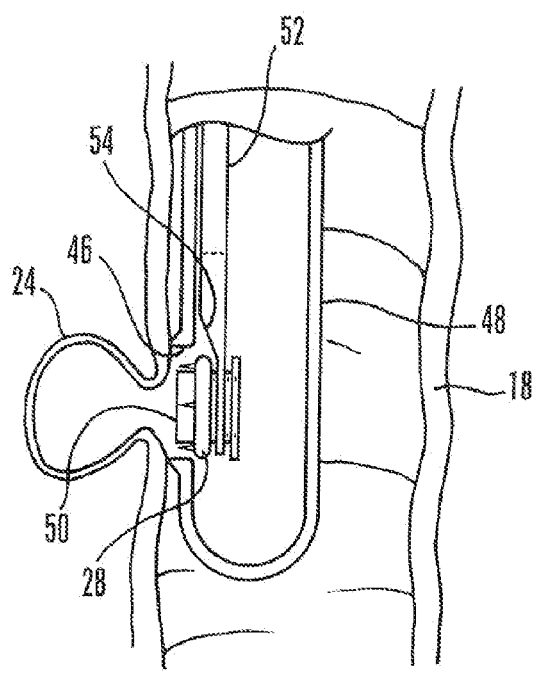
FIGS. 10-15 are side views of an alternate side-access compression ring deployment mechanism showing successive steps of using the alternate mechanism.

Before discussing details of preferred non-limiting compression rings, attention is first drawn to FIGS. 10-15 to illustrate that a compression ring 28 may be advanced out of a side opening 46 of an elongated flexible tube 48 toward a diverticulum 24. As shown in FIG. 10, the compression ring 28 is preloaded in an expanded configuration onto a cylinder 50 in the tube 48. An axially rigid reciprocating actuator rod 52 with ramped surface 54 is disposed in the tube 48 adjacent the cylinder 50.

Figure 11:
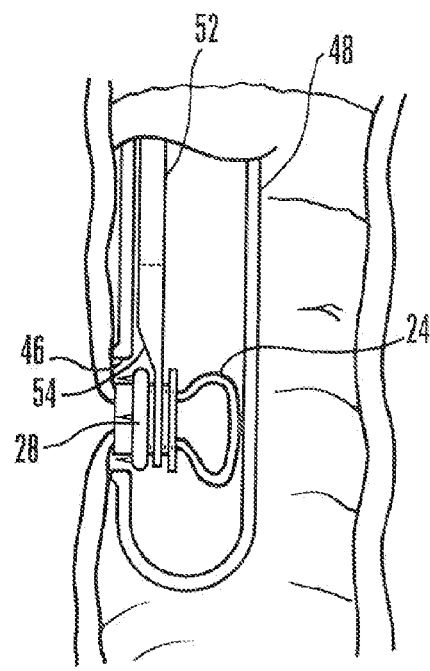
Figure 12:
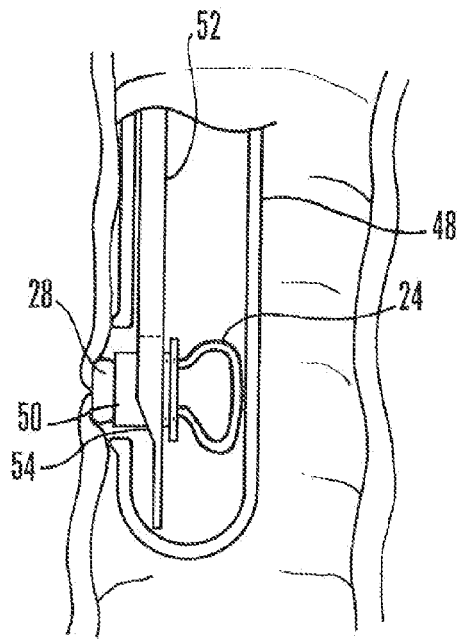

As shown in FIG. 11, the interior of the tube 48 may be evacuated to invert the diverticulum 24 through the cylinder 50 into the colonoscope. Then, as illustrated in FIG. 12 the actuator rod 52 can be moved distally in the tube 48, causing the ramped surface 54 to ride against the compression ring 28, thereby urging the compression ring 28 off the cylinder 50. As the compression ring 28 clears the cylinder 50 it assumes its relaxed, radially smaller configuration around the diverticulum 24 adjacent the colonic wall as shown, compressing the diverticulum 24.

Figure 13:
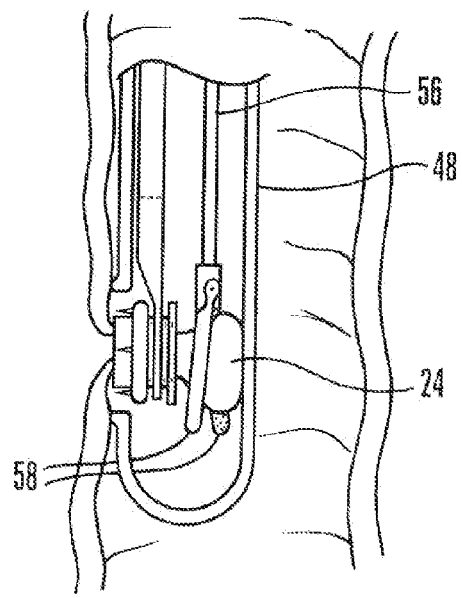

FIG. 13 shows that in addition to or in lieu of vacuum, a grasping device 56 may be advanced in the tube 48 to mechanically grasp and invert the diverticulum 24. The grasping device 56 shown in FIG. 13 has opposed distal pivoting clasping arms 58 that clasp the diverticulum 24 between them. Alternatively, in lieu of clasping arms, the grasping device 56 may have a barbed or pronged distal element to pierce the tissue.

Figure 14:
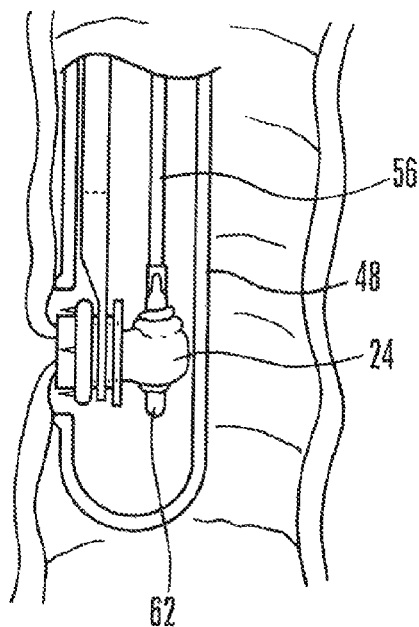
Figure 15:
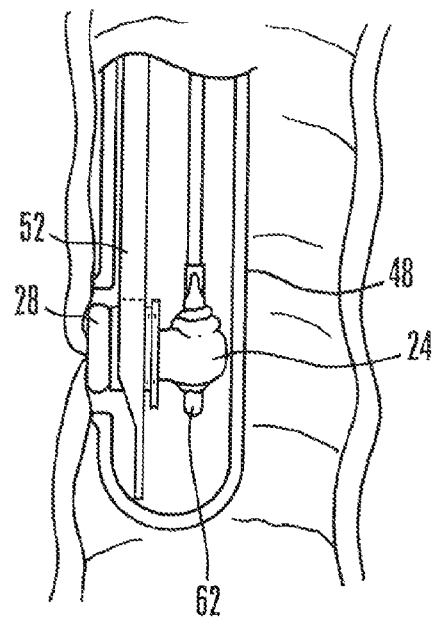

To further effect inversion and serosa to serosa approximation, the grasping device 56 shown in FIG. 14 can have a barbed or pronged distal element 62 that may be twisted to pull the diverticulum 24 into the tube 48. As shown in FIG. 15, once the diverticulum 24 is inverted the actuator rod 52 is operated as described above to push the compression ring 28 onto the diverticulum 24.

Attention is now drawn to various details of embodiments of the compression ring 28. Beginning with FIGS. 16-18, the compression ring 28 includes a resilient expandable plastic or rubber ring-shaped body 64 defining a compression channel 66 that extends axially entirely through the body 64. The body 64 defines a first segment 64a that completely surrounds the compression channel 66 as shown. Also, the body 64 defines a second axial segment 64b that is contiguous to the first axial segment 64a and that also completely surrounds the compression channel 66. The body 64 maybe made of a drug eluting material. The second axial segment 64b can be regarded as a compression ridge that can be formed or molded into the ring, with the radius of curvature of the ridge being established as desired for achieving a desired rate of sloughing. A sharper ridge causes the tissue to slough off faster, while a less sharp ridge allows greater time for serosa to serosa healing prior to sloughing.

When the body is drug eluting material, it can be coated with and then elute drugs such as antiinflammatories, antibiotics, antibacterial drugs, and tissue healing factors. The drug coating can include a bioabsorbable polymer that is loaded with the drug that releases over time.

In one implementation, for example, the body 64 and/or below-described gripping elements such as spikes may be coated with a polymer such as Polyglycolic-Lactic Acid. (PGLA) layers. The layers may be, e.g., bonded to the spikes. The PGLA can be loaded with a carrier drug that elutes as the PGLA absorbs. PGLA can be solubilized in a vapor form by dissolving it in a solvent such as, e.g., dimethyl formamide (DMF). This composition can then have the required drug added, and then sprayed in layer coatings onto the spike or the body. The dosage can be by weight. Furthermore, antimicrobials, anti-inflamatories, heavy weight proteins such as tissue growth factors, etc. may also be mixed into the composition to help with wound healing. The drug eluting coating can be applied with no primer and then heat set onto the spikes or ring.

Figure 16:
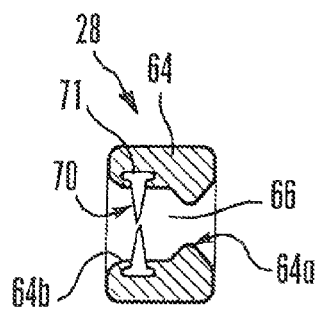
FIG. 16 is a partial cross-sectional view of an example compression ring.

As shown in FIG. 16, one or more axially rigid elongated gripping elements 70 such as spikes extend from the body 64 into the channel 66. The gripping elements 70 may have flatheads 71 as shown to establish a generally "T" shape or, as disclosed below, the heads may be rounded, e.g., hemispherical so that the ring material can impart optimal tissue penetrating force to the gripping elements 71, and to allow the ring material to better control the rotation and orientation of the gripping element 70. The gripping elements 70 may be molded into the body 64.

Figure 17:
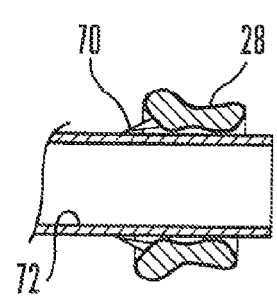
FIG. 17 is a side view of the ring shown in FIG. 16 loaded onto a delivery tube, which could be established by a colonoscope, with the ring shown in cross-section.

In the embodiment shown in FIG. 16 the first axial segment 64a is not engaged with any gripping element 70, while the second axial segment 64b is engaged with the gripping elements 70 by, e.g., embedding or overmolding or otherwise coupling the gripping elements 70 with the second axial segment 64b. The first axial segment 64a may more tightly compress body structure such as diverticulum than the second axial segment 64b. In the non-limiting embodiment shown in FIGS. 16-18, this is effected by making the wall of the first axial segment 64a thicker than the wall of the second axial segment 64b as shown, and more particularly by configuring the first axial segment 64a with a smaller inside diameter than the second axial segment 64b. While FIGS. 16-18 show that the first axial segment 64a and second axial segment 64b are made integrally, they may be separately and juxtaposed with each other.

FIG. 16 shows the compression ring 16 in the relaxed configuration, in which the diameter of the compression channel 66 is relatively small and in which the axial gripping elements 70 are oriented substantially perpendicularly to the axis defined by the body 64. In contrast, FIG. 17 shows the compression ring 28, loaded onto a tube 72 such as the colonoscope 14 discussed above, wherein the configuration of the compression ring 28 is radially enlarged such that the ring 28 closely surrounds the tube 70. In other words, the inside diameter of the compression channel 66 is smaller than the outside diameter of the tube 72 when the ring 28 is in the relaxed configuration, and the ring 28 is deformably stretched such that the inside diameter of the ring 28 is equal to the outside diameter of the tube 72 when the ring is engaged with the tube 72.

Also, in the embodiment shown in FIG. 17, the gripping elements 70 extend in a proximal orientation relative to the body 64 of the ring 28, although as discussed below the elements 70 may be oriented distally. Thus, not only is the ring 28 radially stretched to fit onto the tube 72, but it is twisted about its circumference as well.

Figure 18:
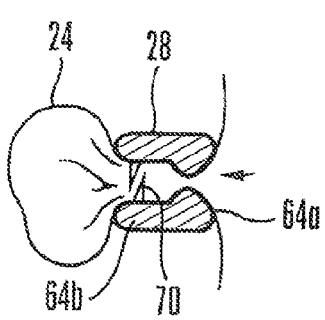
FIG. 18 is a side view of the ring after being pushed off of the tube, with the ring shown in cross-section.

With this in mind, it may be appreciated in reference to FIG. 18 that when the compression ring is pushed off the tube onto, e.g., the diverticulum 24, the ring 28 collapses around the diverticulum 24 as the ring assumes the relaxed configuration, with the diverticulum 24 captured and compressed in the compression channel 66. Furthermore, owing to its material bias the ring 28 twists about its circumference into the relaxed configuration, wherein the gripping elements 70 extend perpendicularly to the compression channel 66, penetrating the tissue as shown in FIG. 18 owing to the hoop strength of the compression ring.

Still further, as mentioned above the first axial segment 64a of the ring 28 grips the tissue more tightly than the second axial segment 64b. Thus, particularly in the case of diverticulum, contaminant substances that might otherwise pass through tissue perforations that may be caused by the gripping elements 70 are sealed from the peritoneum by the tight closure afforded by the first axial segment 64a.

FIG. 19 shows a compression ring 74 with a resilient body defining a substantially continuously tapered inner annular surface 76, with gripping elements 78 being engaged with a wider axial segment of the ring 74 as shown and with no gripping elements 78 being engaged with a narrower axial segment of the ring 74 as shown. The taper of the surface 76 also facilitates loading the ring 74 onto a delivery tube and releasing the ring from the tube. Also, the taper provides a rolling action upon release for driving the gripping elements 78 into tissue.

On the other hand, FIG. 20, which shows only half of a compression ring 80 in cross-section, shows that a first axial segment 82 may be established by a first material and a second axial segment 84 may be established by a second, different material. The second segment 84 is engaged with gripping elements 86. The second material may be softer and/or thinner than the first material, which in any case affords greater compression than the second material. By making the first material (in which the gripping elements 86 are embedded) softer than the second material, the risk of ripping or other damage to the second axial segment 84 from relative motion with the gripping elements 86 when the ring 80 changes configurations is reduced. The two materials may be molded into one compression ring 80 using multiple molding steps.

FIG. 21 shows a compression ring 88 (omitting the gripping elements for clarity) that in all substantial respects may be identical to any of the compression rings discussed above, except that the compression ring 88 may have a flat, rectangular shaped exterior surface 90.

FIGS. 22 and 23 show a compression ring 92 in which four tissue spikes 94 are equidistantly radially spaced and extend into the compression channel, with the ends of the spikes 94 meeting substantially in the center (axis) of the channel. FIG. 24 shows that a compression ring 96 with interior spikes 98 may also be formed around its outer periphery with tabs or tails 100 for facilitating gripping and/or manipulating the compression ring 96 onto a delivery tube.

In another alternate embodiment, FIG. 25 shows a compression ring 102 in which each spikes 104 extends substantially across the diameter of the compression channel formed by the ring 102.

Figure 27:
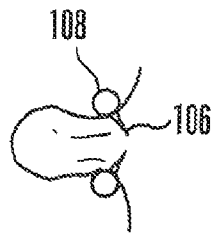
FIGS. 27 and 28 are schematic views showing successive configurations of the ring shown in FIG. 26 as it is pushed onto a diverticulum.
Figure 28:

As discussed above, while the gripping elements of the compression ring may be oriented proximally on the delivery tube, they alternately may be oriented distally as shown in FIG. 26, in which gripping elements 106 of a compression ring 108 are oriented distally on a delivery tube 110. FIGS. 27 and 28 illustrate that when the compression ring 108 is engaged with body structure, the elements 106 rotate to a position in which they are perpendicular to the axis of the ring to penetrate and grip the tissue.

Figure 29:
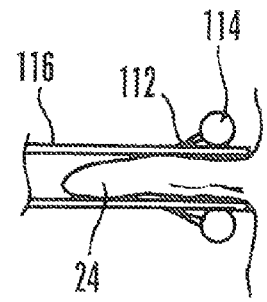
FIG. 29 is a side view of a compression ring loaded onto a delivery tube, with the spikes oriented proximally on the tube.
Figure 30:
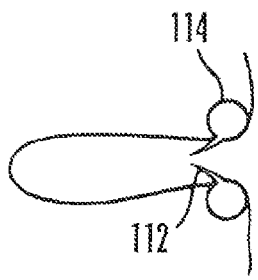
FIGS. 30 and 31 are schematic views showing successive configurations of the ring shown in FIG. 29 as it is pushed onto a diverticulum.
Figure 31:
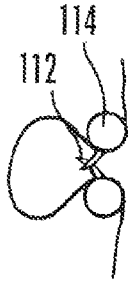

FIGS. 29-31 illustrate the proximal orientation of gripping elements 112 of a compression ring 114 on a delivery tube 116. In this orientation, not only the material bias of the ring 114 but the relaxing action of the diverticulum 24 toward the right in FIGS. 29-31 tend to move the gripping elements 112 back to the perpendicular (relaxed) orientation shown in FIG. 31.

Figure 32:
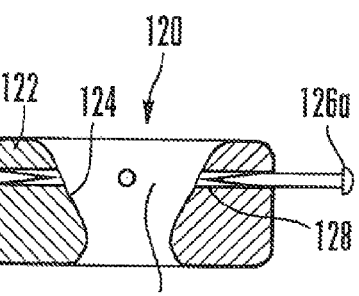
FIG. 32 is a partial cross-sectional view of an alternate compression ring with axially movable spikes.

While the compression rings disclosed above have gripping elements that are affixed within the ring bodies, FIGS. 32-36 illustrate a compression ring 120 with resilient body 122 defining a ramped inside surface 124 in which axially rigid gripping elements 126 can move along their respective axes in respective channels 128 formed in the body 122. As shown in FIG. 32, the gripping elements 126 are initially positioned in a retracted position, in which the gripping elements 126 substantially do not extend into the compression channel 130 of the ring 120. Each gripping element 126 may have a rounded head 126a if desired, and this configuration may be used on any of the gripping elements herein.

Figure 33:
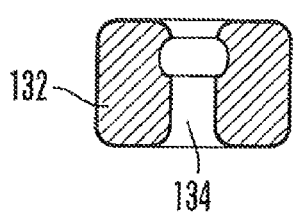
FIG. 33 is a cross-sectional view of an actuating ring to be used to move the spikes shown in FIG. 32.
Figure 34:
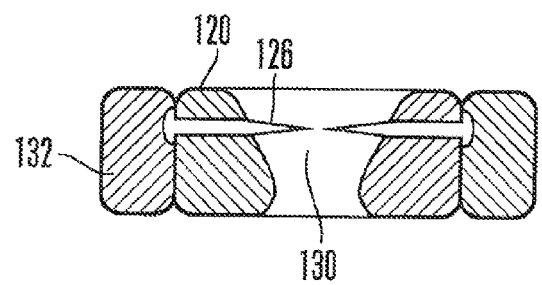
FIG. 34 is a partial cross-sectional view showing the actuating ring surrounding the compression ring to drive the spikes inward.

FIG. 33 shows a resilient actuating ring 132 with central opening 134 for receiving the compression ring 120 therein. The actuating ring 132 can be deformed to an expanded configuration to receive the compression ring 120 coaxially in the opening 134. When the actuating ring 132 is released (FIG. 34) it relaxes to a radially smaller configuration to urge the gripping elements 126 toward an extended position, in which the gripping elements 126 extend into the compression channel 130 to penetrate tissue disposed in the compression channel 130.

Figure 35:
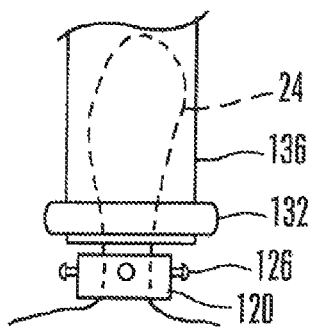
FIG. 35 is a side view showing the compression ring of FIG. 32 pushed onto a diverticulum, with the diverticulum shown in partial phantom.
Figure 36:
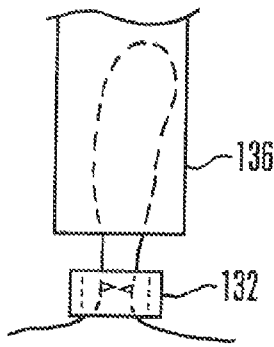
FIG. 36 is a side view showing the actuating ring pushed onto the compression ring, with the diverticulum shown in partial phantom.

FIGS. 35 and 36 further illustrate the above-described operation. With the compression ring 120 delivered over a delivery tube 136 onto tissue such as the diverticulum 24, the actuating ring 132 is held in the expanded configuration on the tube 136 (FIG. 35). The actuating ring is then pushed off of the tube 136 (FIG. 36) to relax onto the compression ring, driving the gripping elements 126 into the diverticulum 24.

As contemplated herein, diverticulum are not the only example of tissue that can be closed off using one of the present compression rings. As shown in FIGS. 37-43, for example, tissue 140 defining a hole 142 can be held together to close the hole. The hole may be a defect in the tissue or a puncture in the tissue or otherwise require closure.

Figure 37:
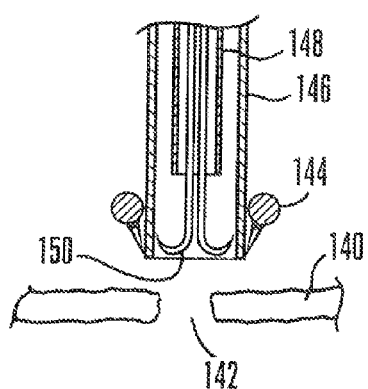
FIGS. 37-43 are schematic side views of an alternate device for closing gastric openings, illustrating-sequential steps in the process.
Figure 38:
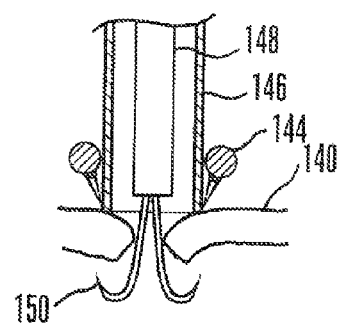
Figure 39:
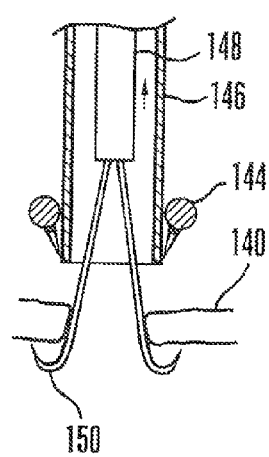
Figure 40:
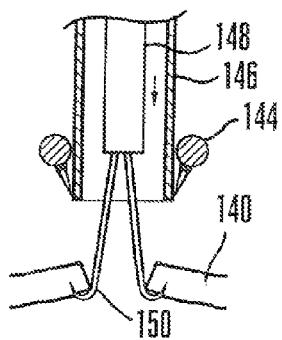
Figure 41:
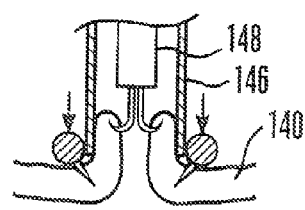
Figure 42:
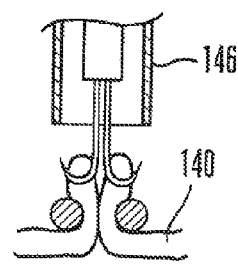
Figure 43:
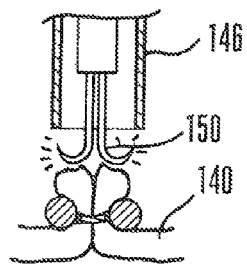

FIG. 37 shows that any one of the above-described compression rings, designated 144 in FIG. 37, may be loaded onto an applicator tube 146 in which a hook control tube 148 is disposed. Plural elongated hooks 150 reciprocate in the hook tube 148. When the applicator tube 146 is advanced to the hole 142, the hook control tube 148 is retracted, the hooks 150 are advanced through the hole (FIG. 38), and once the hook ends dear the hole the hooks 150 under material bias or mechanical actuation expand away from each other (FIG. 39). The hook control tube 148 is advanced (FIG. 40) and the applicator tube 146 advanced to the tissue 140 such that the tissue is pulled (FIG. 41) into the applicator tube 146. The compression ring 144 is then pushed off the applicator tube 146 (FIG. 42) to gather and hold the tissue together, in the case of bowel tissue, serosa to serosa. If desired, electrocautery current can be applied to the hooks 150 (FIG. 43) to release the hooks from the tissue. Or, the hooks may simply be retracted through the tissue. Yet again, the hooks may be made of elastic metal that permits them to straighten when pulled proximally, facilitating removal from the tissue.

Figure 44:
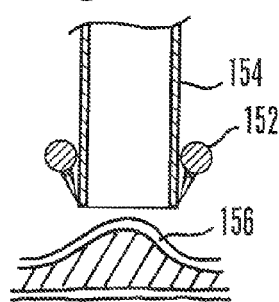
FIGS. 44-46 are side views in partial cross-section showing a hemorrhoid closure device.
Figure 45:
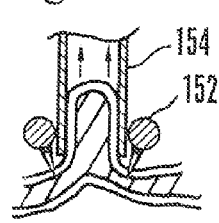
Figure 46:
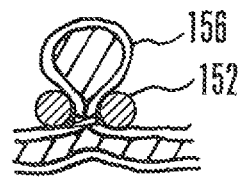

FIGS. 44-46 show that any one of the above-described compression rings, designated 152 in FIG. 44, may be loaded onto a delivery tube 154 to resolve a hemorrhoid 156. The delivery tube 154 can be advanced to the hemorrhoid 156 and the tube evacuated to draw the hemorrhoid into the tube (FIG. 45). The compression ring 152 is then pushed off the tube 154 to surround, compress, and close off the hemorrhoid 156 (FIG. 46).

Figure 47:
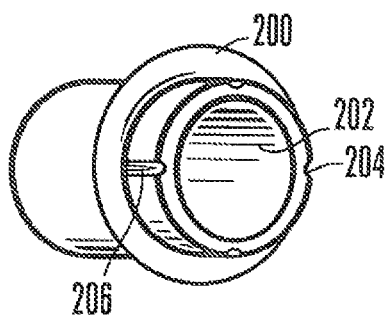
FIG. 47 is a perspective view of a compression ring on an applicator with longitudinal slits to guide the spikes of the ring.

FIG. 47 shows a compression ring 200 expanded onto an applicator 202 that has longitudinal slits 204 formed in its outer surface, such that each spike 206 of the ring 200 can slide in a respective slit 204. The slits maintain the spikes and guide the spikes as the ring is slid off the applicator.

Figure 48:
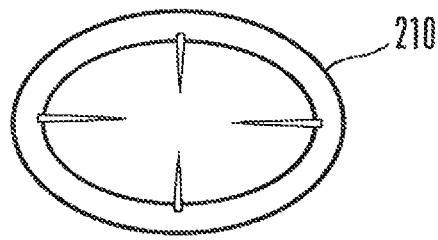
FIGS. 48 and 49 show compression rings that are not circular.
Figure 49:
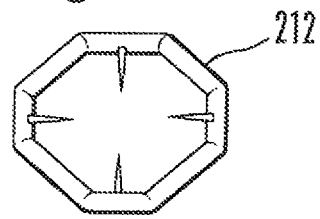

FIG. 48 shows a compression ring 210 that is elliptical as shown, while FIG. 49 shows a compression ring 212 that is octagonal as shown.

Figure 50:
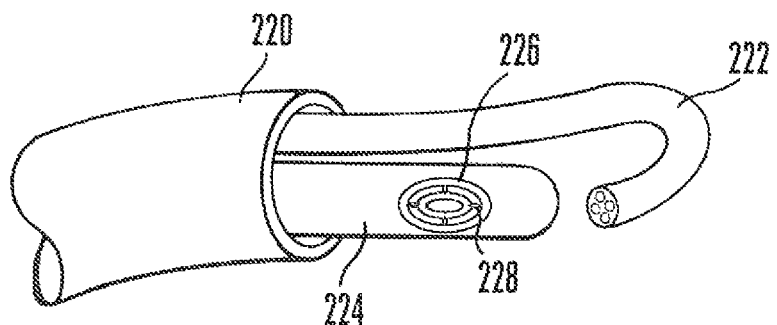
FIG. 50 is a perspective view of a distal portion of a side fire applicator.

FIG. 50 shows that an overtube 220 can be used to deliver an endoscope 222 that can be retroflexed as shown for viewing an applicator 224 with a side opening 226 through which a compression ring 228 can be delivered onto tissue.

If desired, the present compression ring body and/or spikes may be made of absorbable material such as PDS or magnesium so that the spikes could be slowly absorbed by the body over time.

Figure 51:
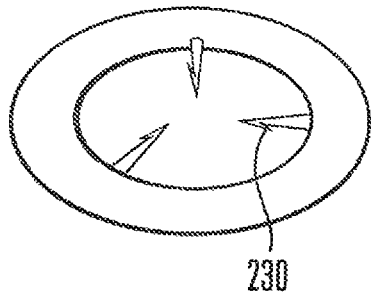
FIGS. 51 and 52 show barbed spikes.
Figure 52:
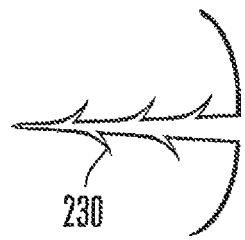

As shown in FIGS. 51 and 52, any of the spikes shown herein can be textured as with one or more quills 230 to better grip tissue. The texturing can be done by mechanical cutting or laser etching to form a fenestrated surface angled in one direction to prevent tissue slippage.

Figure 53:
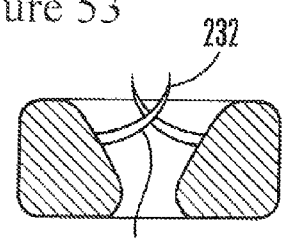
FIGS. 53-55 show curved spikes.
Figure 54:
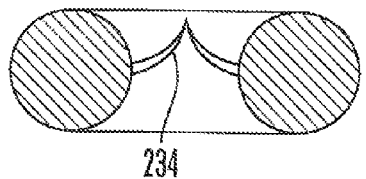
Figure 55:
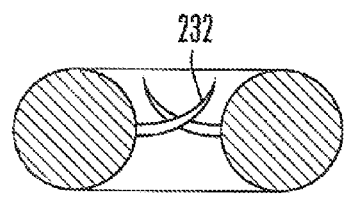

Also, as shown in FIGS. 53-55, any of the spikes herein as shown at 232 can overlap each other and can curve upward with their free ends distanced from the radial plane of the ring when the ring is in the relaxed configuration (FIG. 53) so that the spikes do not unintentionally puncture tissue, moving toward the plane of the ring as shown in FIG. 55 when the ring is stretched. This also provides the ability to use longer spikes that do not pierce the opposite side of the ring from where they are molded, since the spike curve up and away from the radial plane in the relaxed configuration. FIG. 54 shows at 234 that the spikes may be curved but not overlap each other.

Figure 56:
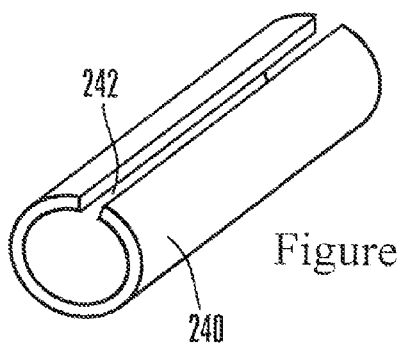
FIGS. 56-58 show various applicators that are not complete cylinders.
Figure 57:
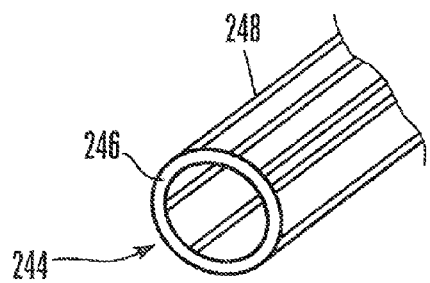
Figure 58:
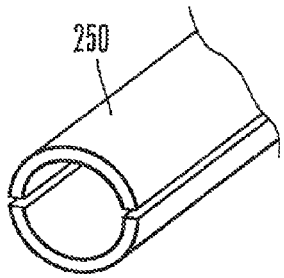

FIGS. 56-60 show that different size applicator tubes or an expandable applicator tube or an incomplete cylinder can be used to allow for expansion of the ring over various sizes of diverticulum. Specifically, FIG. 56 shows a tube 240 that defines about 0.9 of a full cylinder, with a slit 242 being formed in the tube, while FIG. 57 shows an applicator tube 244 that has an end ring 246 connected to plural long thin parallel applicator elements 248 such as rods to define an applicator tube structure. FIG. 58 shows that an applicator tube 250 may be established by two semi-cylindrical halves. Thus, an applicator tube can be a complete cylinder or a partially open cylinder with, e.g., an elongated open slit or even semicircular cross-sectional structure.

Figure 59:
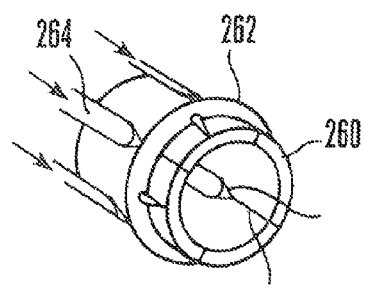
FIG. 59 shows an expandable applicator in a relaxed configuration.
Figure 60:
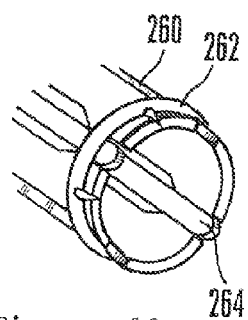
FIG. 60 shows the expandable applicator in an expanded configuration.

FIGS. 59 and 60 show an expandable delivery tube 260 onto which a spiked ring 262 can be mounted, with the tube 260 being expandable as shown in FIG. 6 by means of pushing a cross-bar 264 into the tube's diameter, to accommodate different sizes of diverticulum.

The rings can be loaded onto cartridges that in turn can be removably engaged with an applicator tube one at a time to permit removing a cartridge exhausted of rings and replacing it with a reloaded cartridge.

While the particular DEVICES AND METHODS FOR SECURING TISSUE are herein shown and described in detail, it is to be understood that the subject matter which is encompassed by the present invention is limited only by the claims.

What is claimed is:

1. A method for treating a patient, comprising:
    advancing an applicator into the intestine through a natural orifice to the site of tissue to be removed;
    inverting the tissue at least in part using the applicator; and
    clamping the tissue with a torus-shaped resilient ring defining a central ring axis and a circular transverse axis and having at least one gripping element that engages the tissue, the gripping element being straight from an interface of the gripping element with the ring to a free end of the gripping element and defining a straight element axis from the interface to the free end, the straight element axis being perpendicular to the central ring axis when the ring is in a relaxed state, a distal end of the applicator bearing the ring, the ring being materially biased to the relaxed state, in which the ring assumes a radially smaller configuration, the ring being stretchable to an enlarged state to fit onto the applicator with the gripping element bearing against the applicator to urge the straight element axis away from being perpendicular to the central ring axis and thereby twist the ring about the circular transverse axis, the ring assuming the enlarged state when on the applicator and assuming the relaxed state when urged off the applicator and onto the tissue, the ring being rolled about its circumference onto the delivery device such that upon release of the ring the rings unrolls under the influence of material bias to drive the gripping element into the tissue.

2. The method of claim 1, wherein intestinal wall tissue adjacent the tissue to be removed is held by the ring serosa to serosa.

3. The method of claim 1, comprising:
    preloading the ring onto the applicator; and
    urging the ring off the applicator onto the tissue.

4. The method of claim 3, comprising preloading plural rings onto the applicator.

5. The method of claim 1, wherein the ring is preloaded onto the applicator with the gripping element extending distal of the body.

6. The method of claim 1, wherein the ring is preloaded onto the applicator with the gripping element extending proximal to the body.

7. The method of claim 1, wherein the ring comprises plural gripping elements.

8. The method of claim 7, wherein each gripping element defines an end disposed substantially in the center of the ring when the ring is relaxed.

9. A method for holding tissue together, comprising:
    advancing into a patient through a natural orifice a closure ring including a resilient ring-shaped body defining a compression channel in turn defining a central ring axis and at least one axially rigid elongated gripping element extending from the body into the channel, the closure ring defining a torus shape with a circular transverse cross-section, the gripping element being oriented perpendicular to the central ring axis when the body is in a relaxed configuration;
    engaging the closure ring with body structure such that the gripping element penetrates the body structure and the ring-shaped body surrounds and compresses in the compression channel at least a part of the body structure, wherein the body structure is a hemorrhoid;
    wherein the ring is rolled onto an applicator to twist the ring with the gripping element extending along the applicator against the applicator at an oblique angle to the central ring axis.

10. The method of claim 9, comprising:
    preloading the ring onto an applicator; and
    urging the ring off the applicator onto the body structure.

11. The method of claim 10, comprising preloading plural rings onto the applicator.

12. The method of claim 9, wherein the ring is preloaded onto an applicator with the gripping element extending proximal to the body.

13. The method of claim 9, wherein the ring comprises plural gripping elements.

14. The method of claim 9, wherein the at least one gripping element extends substantially across a diameter of the compression channel.

15. The method of claim 9, wherein each gripping element defines an end disposed substantially in the center of the ring when the ring is relaxed.

16. The method of claim 9, wherein the gripping element includes at least one barb.

* * * * *